United States Patent [19]

Hall

[11] 4,071,407
[45] Jan. 31, 1978

[54] NOVEL MALTASE ENZYME PRODUCED BY A NEW YEAST STRAIN

[75] Inventor: Leo M. Hall, Homewood, Ala.

[73] Assignee: The Board of Trustees of the University of Alabama, Birmingham, Ala.

[21] Appl. No.: 742,240

[22] Filed: Nov. 16, 1976

[51] Int. Cl.$^2$ .................. C12D 13/10; C12K 1/00
[52] U.S. Cl. ........................... 195/62; 195/65; 195/103.5 S
[58] Field of Search ............ 195/62, 65, 66 R, 103.5 S

[56] References Cited

U.S. PATENT DOCUMENTS 4,000,042  12/1976  Adams .................. 195/103.5 S

OTHER PUBLICATIONS

Chiba et al., Agr. Biol. Chem. 37(8) 1831–1836 (1973).
Chiba et al., Agr. Biol. Chem. 37(8) 1823–1829 (1973).

*Primary Examiner*—Lionel M. Shapiro
*Attorney, Agent, or Firm*—Oblon, Fisher, Spivak, McClelland & Maier

[57] ABSTRACT

A maltase enzyme is prepared by growing a strain of Saccharomyces, ATCC 20 488, on a medium containing maltose or malt extract and has been found to be useful in assays for amylase.

14 Claims, No Drawings

NOVEL MALTASE ENZYME PRODUCED BY A NEW YEAST STRAIN

BACKGROUND OF THE INVENTION

1. Field of the Invention

The present invention relates to a new maltase enzyme, its preparation and use in amylase assay procedures.

2. Description of the Prior Art

Prior to the present invention it has been considered that a single strain of the yeast Saccharomyces would produce only a single maltase enzyme Halvorson et al. Biochimica et Biophysica Acta, volume 67, pages 542–553, prepared maltase enzymes from five different strains of the yeast Saccharomyces. Each of these strains produced what appeared to be the same species of maltase (α-glucosidase), since the maltase produced by the process is indistinguishable with respect to heat of inactivation, electrophoretic mobility, chromotography from either CM-cellulose or DEAE cellulose columns, neutralization with specific antiserum and, most importantly, substrate specificity.

One use for maltase has been found to be in testing enzymes for amylase. Amylase assay involves measuring the rate of which the amylase catalyzes the hydrolysis of a substrate into glucose. Typically the measurement is accomplished by use of the maltase enzyme, to convert maltose into glucose. The glucose is then converted to glucose-6-phosphate by reaction with ATP in the presence of the hexokinase enzyme. The glucose-6-phosphate is oxidized in the presence of the glucose-6-phosphate dehydrogenase (Leuconostoc) enzyme to 6-phosphogluconate in the presence of NAD (nicotinamide adenine dinucleotide) which is reduced to NADH (reduced from NAD). The conversion of NAD to NADH changes the absorption of the solution at 340nm. By measuring the change in the absorption, it is possible to measure reaction rate. Diagramatically, using oligosaccharide as the substrate, the process comprises:

| (1) | Oligosaccharide | $\xrightarrow{\text{amylase}}$ | maltose + maltotriose +smaller oligosaccharides |
| (2) | maltose + maltotriose | $\xrightarrow{\text{maltase}}$ | glucose |
| (3) | glucose + ATP | $\xrightarrow{\text{hexokinase}}$ | glucose-6- + ADP phosphate |
| (4) | glucose-6-phosphate + NAD | $\xrightarrow{\text{dehydrogenase}}$ | 6-phosphogluconate + NADH |

The problem encountered in using this amylase assay technique is that previously known maltase enzymes also catalyze the hydrolysis of oligosaccharides to maltose. This reaction was indicative that even when no amylase was present, NAD was, never the less, being converted to NADH which changed the absorption of the solution. The rate of this reaction is called the blank rate. The blank rate must be determined before beginning the amylase assay test and must be accounted for before one can determine how much amylase is present from the reaction kinetics. Since the blank rate introduces a source of potential error, the amylase assay solutions are prepared in a manner such that the blank rate is minimized. This minimization of the blank rate reduces the overall sensitivity of the amylase assay technique.

Accordingly, there exists a need for a method of increasing the sensitivity of amylase assay techniques while simultaneously reducing the blank rate.

SUMMARY OF THE INVENTION

Accordingly, one object of the present invention is to provide an amylase assay technique which has increased sensitivity and a lower blank rate.

Another object of the present invention is to prepare a novel maltase enzyme from a new strain of the yeast Saccharomyces.

These and other objects of the present invention are achieved by growing a strain of Saccharomyces, ATCC 20 488, on a medium containing maltose, maltotriose or malt extract derived from plant sources. The maltase enzyme so produced is recovered and purified. The maltase enzyme thus produced possesses particular utility for amylase assay techniques which employ oligosaccharides as the substrate material.

DESCRIPTION OF THE PREFERRED EMBODIMENTS

A novel strain of yeast, indicated as Saccharomyces, ATCC 20 488 has been isolated from a parent yeast strain after prolonged serial subculture on maltose containing media. This novel strain exhibits ability to produce large amounts of the enzyme maltase (α-glucosidase) when grown either anaerobically or aerobically in a medium containing maltose, maltotriose or malt extract derived from plant sources such as barley malt, corn malt, brewer's wort and the like. The production of the enzyme occurs even if about 10% of the total carbohydrate initially in the growth medium is glucose, so long as maltose, maltotriose or malt extract is also incorporated into the medium. This result is quite surprising as the presence of glucose severaly depresses the formation of the maltase when other strains are used, see Hestrin et al. Arch Biochem Biophys. 29,315 (1950); Nature 168,913 (1951); Spiegelman et al. J. Gen. Physiol. 68,265 (1954); and Robertson et al. J. Gen. Physiol. 73,186 (1957).

Further this new yeast strain exhibits outstanding activity in producing maltase. This new yeast strain has from 3 to 10 times the amount of maltase activity as that reported for other yeast strains.

This novel yeast strain is grown in a growth medium which contains at least one of maltose, maltotriose, or malt extract. Malt extract obtained from various commercial sources may be used, provided that the glucose content does not exceed 10 – 12% of the total carbohydrate and the total maltose plus maltotriose content is 40 – 90% of the total carbohydrate content. The maltose, maltotriose or malt extract may be present in the growth medium in amounts ranging from 25 gms/l to 75 gms/l, preferably from 50 gm/l to 60 gms/l. The growth medium will contain yeast extract, various metal salts and tryptone, peptone, NZ Amine Type A or similar enzymatic digests of casein or meat protein. Tryptone, for example, is a pancreatic digest of casein. It may also be desirable to add anti-foaming agents to prevent the formation of foam, such as silicon oil based agent like Anti-foam A or lard oil based agents.

A suitable growth medium is one which contains yeast extract, tryptone, or peptone, ammonium sulphate, the potassium salt of phosphoric acid, calcium chloride, magnesium sulfate and Antifoam A dissolved in water. The yeast extracts are well-known and are widely used in bacterial studies as a source of naturally occurring B-complex vitamins. One such yeast extract is Bacto Yeast Extract sold by Difco which comprises the water soluble portion of autolyzed yeast This extract is characterized by forming sparkling clean solutions at a concentration of from 0.3 to 0.5 percent at a reaction of pH 6.6. This yeast extract is generally present in amounts ranging from about 1.0 gms/l to about 5 gms/l, preferably from about 2.0 gms/l to about 3.0 gms/l. Tryptone may be present in amounts ranging from about 2.0 gms/l to about 10.0 gms/l, but is preferably present in amounts ranging from about 4.0 gms/l to about 6.0 gms/l. The ammonium sulfate ($(NH_4)_2SO_4$) is generally present in amounts ranging from about 1.0 gms/l to about 4.0 gms/l, but preferably from 1.5 gms/l to about 2.5 gms/l. The potassium phosphate salt ($KH_2PO_4$) is generally present in amounts ranging from about 1.0 gms/l to about 10.0 gms/l, but is preferably present in amounts ranging from about 2.0 gms/l to about 5.0 gms/l. The calcium chloride and magnesium sulfate salts are typically present in amounts ranging from about 0.10 gms/l to about 0.40 gms/l, but, preferably are present in amounts ranging from 0.20 gms/l to about 0.30 gms/l. The pH of the medium may be between 5.3 to 6.8 with a preferred pH of 6.0 to 6.3. During growth of the yeast it is preferable to maintain the pH between 6.0 and 6.3 by the addition of either sodium hydroxide or potassium hydroxide as required.

The yeast is grown in the medium until maximum enzyme activity is observed in samples which are periodically taken from the medium. Any known technique for assaying for enzyme activity may be used.

The temperature of the growth medium is not critical and is typically from about 20° C to about 35° C, but preferably is from about 24° C to about 26° C. The solvent for the growth medium is not critical and may be tap water, deionized water or distilled water since the medium is autoclaved prior to use. The cells are then harvested using conventional techniques such as rapid centrifugation. The enzyme is then released from the cells using a conventional technique. A suitable procedure is described by Halvorson et al. in Biochem, Biophys. Acta. Vol. 30, page 28 (1958) in which the yeast paste is mixed with ethylacetate followed by autolysis after the addition of water and adjustment of the pH to 7.8 with ammoniumhydroxide. A preferred method is to freeze the yeast paste for one day to several months and to release the enzyme from the cells without the use of ethylacetate as follows: The frozen yeast paste is suspended in twice its weight of deionized water. When the paste has thawed, the pH is adjusted to 7.6 – 7.9 with ammonium hydroxide 0.50 to 2.0 M, preferably 1.4 M, and immediately mercaptoethanol in the amount of 7.0 to 7.2 ml/kg yeast is added. The maltase enzyme is released after stirring for 3 to 4 hours.

Other techniques for releasing the enzyme from the cells such as sonication, osmotic shock employing ammoniumphosphate; disintegration by shaking or homogenizing with glass beads; autolysis with toluene; rupture of cells by high pressure passage through an orifice may be used. However, none of these techniques is as convenient or economical as the preferred procedure. Additionally, enzyme yields would be expected to be decreased by many of these procedures.

The released protein is then purified. Conventional protein purification techniques may be used such as ammonium sulfate fractionation, ethanol or acetone fractionation, protamine sulfate treatment, ionexchange chromotography, gel filtration, electrophoresis or adsorption chromotography. One such technique is described by Halvorson et al in Biochem. Biophys. Acta. 30, 28 (1958). Generally these techniques involve fractionation of the protein using several different chromatographic columns. The preferred technique involves fractionation of the protein by successive steps involving removal of nucleic acid by adding an aqueous solution of protamine sulfate having a concentration of from 0.025 to 0.07 gms/ml having a pH of from 6.0 to 7.5, in an amount sufficient to precipitate the nucleic acids, preferably from 4.0 to 6.0 gm of the protamine in solution is added for every liter of protein solution. The resulting protein solution is then fractionated with from 313 to 494 gms of ammonium sulfate per liter. Following the fractionation, the fraction exhibiting maltase activity is dialyzed against a piperazine-HCl buffer solution. The maltase active portions are then collected and subjected to ion exchange chromatography on a DEAE cellulose column. The maltase is eluted from the column by applying a source of chloride ions in a buffer solution such as 0.02 M piperazine - HCl buffer, having a pH of from 6.0 to 7.0. The fraction exhibiting a maltase activity greater than 300,000 units/500 ml are collected. These collected fractions are then subjected to absorption chromatography on hydroxylapatite. The active maltase fractions are then collected. The purified maltase may be stored at 4° C as a suspension in 75% saturated ammonium sulfate, or as a dry powder after lyophilizing the maltase which is dissolved in water, or in a dilute, 0.01 - 0.05 M buffer at approximately neutral pH, pH 6.5 – 7.5. A phosphate buffer is preferred, but other buffers may be used if desired.

An alternative and less preferred technique when cells are disrupted with ethyl acetate, involves removal of cell debris by centrifugation or filtration, removal of nucleic acids by protamine treatment, and passage of the protein extract through a column of sephadex G-25 equilibrated with piperazine-HCl buffer. The emergence of protein is monitored at 280 nm and fed directly onto a column of DEAE cellulose which is connected in series with a column packed with hydroxylapatite. The maltase is then eluted from the hydroxylapatite column using a phosphate buffer. The eluted material is then fractioned on a DEAE cellulose column. This final fractionation involves first passing the material through a column of Sephadex G-25 and then the eluate is passed through the DEAE-cellulose column. The active peaks are then collected. The flow rates and other parameters are not critical. These parameters will depend on the amount of material being fractioned and on column size and may be readily determined.

These purification techniques remove extraneous materials such as ethanol, ethylacetate, salts, peptides, nucleic acids, materials present in the growth culture medium, alcohol dehydrogenase, aldehyde dehydrogenase, hexokinase, glucose-6-phosphate dehydrogenase, proteases, and NADH oxidase, and other proteins. Since the new yeast strain is free of α- and β-amylases, it was not necessary to develope the procedure for their removal.

The maltase produced from the novel strain of Saccharomyces exhibits a number of properties not possessed by maltase prepared using other strains of yeast. In particular, the maltase activity exhibited is not that of single species of enzyme. For example, chromatography on diethylaminoethyl cellulose (DEAE) yields at least two forms of enzyme and under proper conditions at least three forms of the enzyme are discernible. Adsorption chromatography on hydroxylapatite reveals that two major novel forms of maltase are produced by the novel yeast strain. Electrophoresis of enzyme extracts on cellulose acetate reveals multiple forms of active enzyme with at least six distinguishable forms of the enzyme being discernible. Chromatography of the maltase isolated from the new yeast strain on carboxymethyl cellulose under conditions similar to those employed by Halvorson et al reported in Biochem. and Biophys. Acta, Volume 67, pages 42–53 (1963) has shown that the enzyme is not absorbed by the ion exchanger. It had been expected, based on Halvorson's work, that the maltase would have been absorbed by the carboxymethyl cellulose. Since it was not absorbed this demonstrates that the maltase from the novel strain of yeast must be different from previously reported maltase from other strains of Saccharomyces. This behavior lends further support to the conclusion that the yeast strain and maltase produced by it are unique.

The novel maltase enzyme produced by the novel strain of Saccharomyces will hydrolyze phenyl-α-D-glucoside, p-nitrophenyl-α-D-glucoside, p-nitrophenyl-α-D-maltoside and sucrose. Of particular importance is the specificity of this maltase in hydrolyzing maltose, maltotriose, maltotetraose, maltopentaose and the higher oligosaccharides. This maltase enzyme hydrolyzes each of these carbohydrates at a different rate. For example, maltotetraose is hydrolyzed only 1/100 as fast as maltose; maltopentaose is hydrolyzed only 1/500 as fast as maltose and the higher oligosaccharides are hydrolyzed at rates less than 1/1000 as fast.

This property permits the use of the enzyme in an amylase assay test employing the larger oligosaccarides such as maltopentaose, maltohexaose, maltoheptaose, maltoactaose, matononaose, and the like. The novel maltase may also be used in amylase assay tests employing chromogenic and fluorogenic derivatives of the oligosaccharides, such as α-D-glycosides of nitrophenol, umbelliferone, fluorescein, and the like, with maltotetraose, maltopentaose, maltohexaose, maltoheptaose, maltoactoase, and the like. The amylase will cleave these derivatives to maltose - or maltotriose-glycosides which in turn would be hydrolyzed to free aglycon and glucose, yielding the chromogenic and fluorescent compounds.

The maltase is used to hydrolyze the smaller oligosaccharides (i.e. maltose and maltotriose) produced by the action of amylase on the substrate to glucose. The glucose may then be measured by a variety of techniques such as the use of glucose oxidase, peroxidase and a suitable chromagen such as o-dianisidine; measurement of glucose using glucose oxidase and an oxygen electrode; the use of hexokinase, and glucose-6-phosphate dehydrogenase in the presence of ATP, NAD, (or NADP) and Mg$^{++}$: The extent of the reaction could also be measured by the use of reagents to detect an increase in the reducing properites of the solution. Such reagents include dinitrosalicylic acid in alkaline solution; copper reduction methods using neocuproine-copper solution and the like.

A particularly preferred amylase assay technique involves the following reaction sequence:

| | | | |
|---|---|---|---|
| 1. | oligosaccharide | $\xrightarrow{\text{amylase}}$ | maltose + maltotriose smaller oligosaccharides |
| 2. | maltose + maltotriose | $\xrightarrow{\text{maltase}}$ | glucose |
| 3. | glucose + ATP | $\xrightarrow{\text{hexokinase}}$ | glucose-6-phosphate + ADP |
| 4. | Glucose-6-phosphate + NAD | $\xrightarrow{\text{glucose-6-phosphate dehydrogenase}}$ | 6-phospho-gluconolactone + NADH |

The change in the absorbance at 340 nm is taken as a measurement of amylase activity. The amylase assay solution used in the above technique would typically have the following composition: Hexokinase 0.5 to 10 I.U./ml, preferably 2.5 – 3.0 I.U. ml. Glucose-6-phosphate dehydrogenase 0.5 to 10 I.U./ml, preferably 2.5 – 3.0 I.U./ml. Magnesium acetate or magnesium chloride at from 001 to .02 M, preferably .002 to .003 M. NAD 0.5 to 5.0 mg/ml, preferably 2.0 to 3.0 mg/ml Na$_2$ATP .2H$_2$O 0.20 to 2.0 mg/ml, preferably 0.4 to 0.6 mg/ml as the ATP source, maltase 100 to 400 units/ml, preferably 200 to 250 units/ml.

ATP is the abbreviation for adenosine triphosphate. Maltase units are as defined in this application as the absorbance change at 400 nm using p-Nitrophenyl glucoside as the substrate. 1.0 unit is equivalent to an absorbance change of 1.00 per min. at 38° in a 1 cm cell. containing 1.00 ml the following solution:

Potassium phosphate buffer, 0.10 M, pH 6.8, p-nitrophenyl-α-D-glucoside, 500 mg/l, mercaptoethanol 0.10 ml/liter. A phosphate buffer such as sodium phosphate or potassium phosphate is used because its pKa closely matches the optimum pH of amylase and maltase activity. The concentration of the buffer may range from 0.02 to 0.20 molar, but is preferably from 0.08 to 0.12 M. The pH may range from 6.5 to 7.1, but is preferably from 6.8 to 7.0.

Chloride ions are known to activate the amylase and may be added to the solution if desired. If used, the chloride ion concentration should range from 0.030 to 0.20 M, but is preferably about 0.04 to 0.06 M. The chloride ions may be supplied by any convenient source such as KCl, NH$_4$Cl or NaCl, but is preferably added as NaCl.

The oligosaccharide content of the solution may range from 0.5 to 10 mg/ml but is preferably from about 3 to about 4 mg/ml. The oligosaccharides which may be used include:

| | |
|---|---|
| maltopentaose | maltooctaose |
| maltohexaose | maltononaose |
| maltoheptaose | maltodecaose and larger | but it is preferred to use maltopentaose through maltodecaose.

When other techniques for measuring glucose are used the conditions typically employed in the prior art are used. The substitution of the maltase enzyme for those previously used does not necessitate any changes in the techniques used to measure the glucose.

Having generally described the invention, a more complete understanding can be obtained by reference to certain specific examples, which are included for purposes of illustration only and are not intended to be limiting unless otherwise specified.

EXAMPLE 1

The novel strain of Saccharomyces was grown to prepare the novel maltase. The growth media had the following composition:

The following are dissolved in 1000 ml of tap water and autoclaved:

| | | |
|---|---|---|
| Yeast extract | 2.5 gm | |
| Tryptone or Peptone | 5.0 gm | |
| $(NH_4)_2SO_4$ | 2.0 gm | Antifoam A is added routinely. |
| $KH_2PO_4$ | 2.0 gm | |
| $CaCl_2 . H_2O$ | 0.25 gm | |
| $MgSO_4 . 7H_2O$ | 0.25 gm | |

To 20 liters o the above medium, just before innoculation with a seed culture, 2.5 lbs. malt extract is added. A 1 liter seed culture grown on the above medium except for the addition of 40 gms of maltose hydrate per liter is used to innoculate the growth medium. The seed culture is grown for 24 hours.

The yeast are grown at 25°–27° C with gentle stirring or with aeration to prevent settling of the yeast. The progress of the culture is followed by measurement of turbidity of the yeast suspension and also by measurement of maltase activity in the cells. After growth to maximal enzyme activity the cells are harvested by rapid centrifugation. The packed cell mass may then be processed according to the technique of either Example 2 or Example 3.

EXAMPLE 2

The packed wet cell mass (wet weight 100–200 gms) is stirred with 40 ml of ethyl acetate at room temperature for 45 minutes. 400 ml of deionized water is added and the pH adjusted with 1M $NH_4OH$ to 7.6 – 7.7. Immediately after adjustment of the pH, 1.0 ml of mercaptoethanol is added. Release of the enzyme from the cells is complete after standing at room temperature for 4 hours. The enzyme is quite stable at this and subsequent stages. For example, negligible loss of activity is observed after 24 hours at room temperature or after 96 hours at 4° C. The supernatant obtained after centrifugation at 8000 × g for 15 minutes is taken for subsequent purification steps. If necessary, the pH is adjusted to 6.2 – 6.4 with $NH_4OH$.

Purification Procedure:

Step. 1. To the yeast extract, thus obtained, at 4° C was added 1.0 gm of protamine sulfate dissolved in 50 ml of warm deionized water and adjusted to pH 6.2 with 1 M $NH_4OH$. After standing for 1–2 hours centrifuge and retain the supernatant for Step 2.

Step 2. The supernatant is passed through a column of Sephadex G-25 at room temperature equilibrated with buffer of the following composition:

NaCl    0.01 M
HCl     0.01 M

The pH of the above solution is adjusted to 6.2 with 1.0 M piperazine hexahydrate, the volume adjusted and 0.10 ml of mercaptoethanol added per liter of buffer. The emergence of protein is monitored at 280 nm and collected.

Step 3. The eluate containing protein of Step 2 is fed directly onto a column of DEAE cellulose (Whatman DE 32, bed volume 50 ml, 2.2 × 13 cm) equilibrated with the buffer described in Step 2. This column is connected in series to the inlet of a column of hydroxylapatite (BioRad Bio-Gel, HT, bed volume, 200 ml, 4.5 × 12.6 cm) which has been equilibrated with 0.02 M potassium phosphate buffer, pH 6.7 containing 0.1 ml of mercaptoethanol per liter. Once all of the protein has entered the DEAE column (flow rate not critical; 2–3 ml per minute) the column is washed with 200 ml of buffer of the following composition to elute that portion of the maltase absorbed to the DEAE:

Nacl    0.066 M
HCl     0.033 M

Adjusted to pH 6.2 with piperazine hexahydrate and containing 0.1 ml of mercaptoethanol per liter.

Step. 4. The DEAE column is disconnected and the hydroxyl apatite column eluted with phosphate buffer as follows:

A. 0.08 M potassium phosphate, pH 6.7, containing 0.1 ml of mercaptoethanol per liter. 400 ml of buffer elutes inert protein which is discarded.

B. 0.16 M potassium phosphate, pH 6.7, containing 0.1 ml of mercaptoethanol per liter. A major protein peak is eluted containing essentially all of the maltase activity. Volume of active fraction is 150 ml.

The flow rate in this elution at room temperature is not critical, 2–3 ml per minutes is ordinarily employed. The fractionation at room temperature is particularly important as fracionation at 4° C leads to considerable band spreading and poor recovery of activity.

Step. 5. The active fraction of step 4 is passed through a Sephadex G-25 column as before in Step 2. The eluate containing protein is passed onto a DEAE cellulose column (Whatman DE 32, bed volume 100 ml, 3.0 × 14.2 cm) equilibrated with the buffer described in Step 2.

The following buffers are prepared in mixing vessels, 250 ml of each solution is prepared.

| I | II |
|---|---|
| Buffer as in Step 2 | NaCl 0.10 M<br>HCl 0.05 M<br>Adjusted to pH 6.2 with piperazine<br>0.10 ml of mercaptoethanol per liter |

Before elution the column is washed with 200 ml of buffer I. The active enzyme is eluted by changing the Cl-concentration of the buffer and emerges from the column at approximately 0.06 M Cl, calculated for the delivery to the column. Only two major peaks of protein are eluted, which overlap and both contain maltase activity. The smaller peak represents 20% of the total active enzyme eluted. Both peaks are useable for the amylase test. An NADH "OXIDASE" elutes just prior to the minor peak activity of maltase and must be excluded. Total volume of eluate containing maltase from both peaks of activity is 170 ml.

The recovery and yield of the maltase is shown in the following table:

| Step | Maltase Activity | % Recovery |
|---|---|---|
| Initial extract Step 1 | 480,000 | 100 |
| Step 2 | 470,000 | 98 |
| Step 3 | 465,000 | 97 |
| Step 4 – 5 | 408,000 | 85 |
| Step 6 | 390,000 | 81 |

The final yield of protein is 250–300 mg, determined by absorbance at 280 nm.

EXAMPLE 3

The novel strain of Saccharomyces was grown on the medium in the same manner as in Example 1. The yeast was harvested by rapid centrifugation when assay of the culture for maltase indicated that the maltase activity was maximal. The yeast paste was stored in the frozen state until use. The maltase in the yeast paste was extracted and purified as follows:

Step I. 6.3 kg frozen yeast paste was added to 12.7 kg water and stirred until the yeast was thawed. The pH of the slurry was adjusted to 7.7 by the slow addition of 1.4M ammonium hydroxide, and 45 ml of mercaptoethanol were added. The suspension was stirred an additional 4 hours to release the maltase quantitatively.

Step II. To the suspension 52 gm of protamine sulfate dissolved in 900 ml of water and adjusted to a pH of 6.2–6.7, was added with stirring to precipitate nucleic acids. After standing at 4° C for 18 hours, insoluble material was removed by filtration after the addition of Celite as a filter aid. Assay of the filtrate indicated 21,000,000 units of maltase enzyme were present.

Step III. The pH of the filtrate was adjusted to 6.7–6.8 with 1.4 M ammonium hydroxide and solid ammonium sulfate was added to 50% saturation. After stirring for 2 to 3 hours, 250 gm of Celite were added and the precipitate was removed by filtration and discarded. To the filtrate additional solid ammonium sulfate was added to achieve 72.5% saturation in order to precipitate the maltase. After stirring for an additional 3 hours the maltase was collected by centrifugation. Total activity recovered was 19,800,000 units.

Step IV. The ammonium sulfate precipitated maltase was dissolved in 600 ml of 0.25 M piperazine-HCl buffer, pH 6.2 and dialyzed against three 20 liter portions of 0.02 M piperazine HCl buffer containing 0.1 ml of mercaptoethanol per liter, pH 6.2, at 4° C during a four day period. At the end of the dialysis a voluminous precipitate was removed by centrifugation and discarded. Recovery of maltase was 16,800,000 units.

Step VI. The dialyzed solution of maltase was treated in the cold (4° C) with 230 gm of moist DEAE cellulose to remove contaminating chromagens and undesired protein. After removal of the DEAE by filtration, the solution was applied to a chromatographic column containing 6 liters of DEAE cellulose equilibrated with 0.02 M piperazine-HCl buffer containing 0.10 ml of mercaptoethanol liter, pH 6.2, 4° C. After the enzyme solution was delivered to the column, the column was washed with 6 liters of 0.01 M piperazine-HCl buffer, pH 6.2. Maltase was eluted from the colunn upon application of a linear gradient of chloride ions in piperazine-HCl buffer. The gradient increased from 0.02 M to 0.30 M chloride in a total volume of 16 liters. Fractions of 500 ml each were collected and those fractions containing greater than 300,000 units of maltase were combined. Recovery of maltase was 15,800,000 units.

Step VII. The maltase containing solution was degassed at room temperature by the application of a moderate vacuum and was introduced at room temperature into a 6 liter bed of hydroxylapatite in a chromatographic column previously equilibrated with 0.01 M potassium phosphate buffer, pH 6.8, containing 0.10 ml of mercaptoethanol / liter. The column was washed stepwise with phosphate buffers of increasing molarity, each containing 0.02% sodium azide and 0.10 ml of mercaptoethanol/liter as follows:

| 0.02 M | 6 liters |
|---|---|
| 0.08 M | 6 liters |
| 0.25 M | 8 liters. |

Maltase activity was eluted in two separate peaks with 0.08 M and with 0.25 M phosphate buffer, respectively. These two distinct froms of enzyme have been named Peak I Maltase and Peak II Maltase, respectively. The recovery of maltase activity was 4,200,000 and 8,140,000 units for Peak I and Peak II, respectively.

Step III. The maltase was precipitated from the fractions eluted from the hydroxyapatite column by the addition of solid ammonium sulfate to 75% saturation. The precipitate was collected by centrifugation and was stable upon storage in the cold (40° C) for at least several months.

The two forms of maltase can each be used in the amylase assay described in Example 4. However, Peak II maltase is preferred since the sensitivity of the amylase test is increased by about 4 fold compared to when Peak I maltase is used.

The purified enzyme recovered by either technique is stable in solution (piperazine-HCl or phosphate buffer pH 6.2 to 6.7 respectively) at 4° C for at least two weeks with less than 5% decline in activity. Bacterial contamination may be controlled by the addition of 0.1% sodium azide. The purified enzyme is stored as a lyophillized dry powder after buffer exchange of the eluate from the last step of th purification procedure using a Sephadex G-25 column equilibrated with 0.01 M potassium phosphate, pH 6.7. The dry powder is stable at −20° C for at least 6 months.

The hydroxylapatite may be used repeatedly after regeneration with 0.5 M potassium phosphate buffer, pH 6.7, followed by equilibration with the dilute phosphate buffer listed.

The DEAE cellulose may be used repeatedly after suspension in 0.5 M NaOH, washing with $H_2O$, suspension in 0.5 M HCl, washing with $H_2O$, and equilibration with the starting piperazine-HCl buffer.

EXAMPLE 4

A comparison of the effectiveness of the novel maltase in an assay system with two yeast maltase preparations commercially available clearly demonstrate the superiority of the new maltase, as indicated in the Table.

TABLE I

Blank rate and sensitivity of amylase using the novel maltase and commercially available maltases.

| Type of Maltase | Blank[1] Rate mA/min[3] | Rate after addition[2] of serum amylase mA/min |
| --- | --- | --- |
| Novel maltase Peak II | 1.5 | 21.5 |
| Commercial Maltase source A | 23.5 | 39.4 |
| Commercial Maltase Source B | 30.7 | 51.0 |

[1]The rate of absorbance change was determined at 340 nm, 37° C in the absence of added serum amylase.
[2]The rate of absorbance change was determined after the addition of 10 ul of normal serum to 1.00 ml of amylase reagent.
[3]The absorbance changes are expressed as milliabsorbance per minute.

The assays were made with a reagent of the following composition: potassium phosphate buffer, 0.10 M, pH, 6.9; NaCl, 0.05 M; magnesium acetate, 0.0025 M; NAD, 2.0 mg/ml; ATP, 0.50 mg/ml; oligosaccharide (see co-pending application Serial No. 730,820, filed 10/7/76) 3.5 mg/ml; hexokinase, 2.50 IU/ml; and glucose-6-phosphate dehydrogenase from Leuconostoc, 2.5 IU/ml. The maltase activity in each experiment was identical at 250 Units/ml.

The data presented in Table I demonstrates that the use of the novel maltase in amylase assays greatly improves the signal to noise ratio. Thus, with the novel amylase the signal to noise ratio was 14.3, while with commercially available maltases this ratio was 1.68 or 1.66 when 10 μl of normal serum was assayed. This property of the novel amylase permits one to measure amylase in small quantities of biological fluids with increased accuracy and precision, and eliminates the need for blank rate corrections in determining the amylase activity of samples. This data also supports the conclusion that the novel maltase has properties uniquely different from prior art maltase.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. Maltase enzyme characterized by hydrolyzing maltotetraose only about 1/100 as fast as maltose and maltopentaose only about 1/500 as fast as maltose and prepared by growing a strain of Saccharomyces, ATCC 20,488, in a growth medium containing at least one of maltose, maltotriose or malt extract derived from a plant source, releasing the enzyme from the yeast cells, and recovering the enzyme.

2. The enzyme of claim 1, which is free of nucleic acids, α-and β-amylase, ethanol, ethylacetate, salts, peptides, alcohol dehydrogenase, aldehyde dehydrogenase, hexokinase, glucose-6-phosphate dehydrogenase, protease, NADH oxidase, and other proteins.

3. A process for prepaing a novel maltase enzyme which comprises growing a novel strain of Saccharomyces, ATCC 20 488, in a growth medium which comprises at least one of maltose, maltotriose or malt extract derived from a plant source.

4. The process of claim 3 wherein the growth medium contains a malt extract derived from a plant source.

5. The process of claim 3 wherein the growth medium contains a yeast extract, tryptone, and ammonium phosphate.

6. The process of claim 3, wherein the enzyme is recovered by centrifuging a growing medium.

7. The process of claim 3, wherein from 2.5 gms/l to 75 gms/l of at least one maltose, maltotriose or malt extract derived from a plant source is present.

8. The process of claim 7, wherein the growing medium also contains about: 2 to 10 gms/l of tryptone; 1.0 to 4.0 gms/l of $(NH_4)_2SO_4$; 1 to 10 gms/l of $KH_2PO_4$; 0.10 to 0.40 gms/l of $CaCl_2$ and 0.10 to 0.40 gms/l of $MgSO_4$.

9. The process of claim 3, wherein an anti-foaming agent is added to the growth medium.

10. The process of claim 8 whrein from 50 to 60 gms/l of at least one of maltose, maltotriose or a malt extract derived from a plant source is present.

11. The process of claim 10 wherein a malt extract derived from a plant source is present in the growth medium.

12. In a method of assaying for the enzyme amylase in a sample by:
  a. introducing the sample into an assay solution comprising an oligosaccharide and maltase; and
  b. measuring the rate at which glucose is formed in the assay solution; the improvement which comprises using as the maltase, the maltase of claim 1.

13. The method of claim 12, wherein the assay solution also comprises hexokinase, glucose-6-phosphate dehydrogenase, adenosine triphosphate, and nicotinamide adenine diniicleotide.

14. The method of claim 13, wherein the change in absorbance at 340 nm of the sample containing assay solution is taken as the measurement of amylase activity.

* * * * *

UNITED STATES PATENT AND TRADEMARK OFFICE
CERTIFICATE OF CORRECTION

PATENT NO. : 4,071,407
DATED : January 31, 1978
INVENTOR(S) : Leo M. Hall

It is certified that error appears in the above-identified patent and that said Letters Patent are hereby corrected as shown below:

Column 10, line 11, delete "0.01" and insert --0.02--;

line 33, delete "40°C" and insert --4°C--;

line 47, delete "th" and insert --the--.

Signed and Sealed this

Third Day of April 1979

[SEAL]

Attest:

RUTH C. MASON
Attesting Officer

DONALD W. BANNER
Commissioner of Patents and Trademarks